(12) United States Patent
Kelsch et al.

(10) Patent No.: US 9,931,513 B2
(45) Date of Patent: Apr. 3, 2018

(54) FEED-THROUGH CONNECTOR ASSEMBLY FOR IMPLANTABLE PULSE GENERATOR AND METHOD OF USE

(75) Inventors: Daniel N. Kelsch, Fairview Park, OH (US); Alexander K. Smith, Chesterland, OH (US)

(73) Assignee: Nuvectra Corporation, Plano, TX (US)

( * ) Notice: Subject to any disclaimer, the term of this patent is extended or adjusted under 35 U.S.C. 154(b) by 1231 days.

(21) Appl. No.: 13/359,954

(22) Filed: Jan. 27, 2012

(65) Prior Publication Data

US 2012/0246921 A1 Oct. 4, 2012

Related U.S. Application Data

(63) Continuation-in-part of application No. 13/074,358, filed on Mar. 29, 2011, now Pat. No. 8,369,951.

(51) Int. Cl.
| | |
|---|---|
| *A61N 1/375* | (2006.01) |
| *A61N 1/04* | (2006.01) |
| *A61N 1/05* | (2006.01) |
| *H01R 43/20* | (2006.01) |
| *H01R 43/027* | (2006.01) |
| *H01R 13/40* | (2006.01) |
| *H01R 13/52* | (2006.01) |

(52) U.S. Cl.
CPC ............. *A61N 1/3752* (2013.01); *A61N 1/04* (2013.01); *A61N 1/05* (2013.01); *H01R 43/20* (2013.01); *H01R 13/40* (2013.01); *H01R 13/5224* (2013.01); *H01R 43/027* (2013.01); *Y10T 29/49117* (2015.01); *Y10T 29/49147* (2015.01)

(58) Field of Classification Search
CPC .... A61N 1/3752; H01R 43/20; H01R 43/027; H01R 13/40; H01R 13/5224; Y10T 29/49147; Y10T 29/49117
See application file for complete search history.

(56) References Cited

U.S. PATENT DOCUMENTS

| 4,469,104 A | 9/1984 | Peers-Trevarton |
| 4,995,389 A | 2/1991 | Harris |
| (Continued) | | |

FOREIGN PATENT DOCUMENTS

| DE | 19917779 | 11/2000 |
| EP | 1062986 | 12/2000 |
| (Continued) | | |

OTHER PUBLICATIONS

Partial European Search Report; Application No. EP 15 15 7480; Place of Search: Munich; Date of Completion of Search: Apr. 30, 2015.

(Continued)

*Primary Examiner* — Peter DungBa Vo
*Assistant Examiner* — Jeffrey T Carley
(74) *Attorney, Agent, or Firm* — Haynes and Boone, LLP; Eric Li

(57) ABSTRACT

A connector assembly, and its method of assembly, for use in a medical device for connecting an IPG to a connector assembly for connecting the IPG to a relatively large plurality of electrodes that can support 24 or more stimulation channels for stimulating one or more stimulation regions of a patient. Also the IPG and the stimulation system and the stimulation therapy utilizing the connector assembly.

21 Claims, 15 Drawing Sheets

(56) References Cited

U.S. PATENT DOCUMENTS

| | | |
|---|---|---|
| 5,545,188 A | 8/1996 | Bradshaw et al. |
| 5,795,165 A | 8/1998 | Jarl |
| 5,899,930 A | 5/1999 | Flynn et al. |
| 6,205,358 B1 * | 3/2001 | Haeg ............ A61N 1/375 29/857 |
| 6,498,952 B2 | 12/2002 | Imani et al. |
| 6,654,641 B1 | 11/2003 | Froberg |
| 6,662,035 B2 | 12/2003 | Sochor |
| 6,749,358 B2 | 6/2004 | Balsells |
| 6,878,013 B1 | 4/2005 | Behan |
| 6,895,276 B2 | 5/2005 | Kast et al. |
| 6,895,876 B2 | 5/2005 | Bergere et al. |
| 7,070,455 B2 | 7/2006 | Balsells |
| 7,195,523 B2 | 3/2007 | Naviaux |
| 7,274,963 B2 | 9/2007 | Spadgenske |
| 7,537,474 B2 | 5/2009 | Deininger et al. |
| 7,654,843 B2 | 2/2010 | Olson et al. |
| 7,690,953 B2 | 4/2010 | Boyd et al. |
| 7,711,427 B2 | 5/2010 | Janzig et al. |
| 7,769,458 B2 | 8/2010 | Ries et al. |
| 7,890,175 B1 | 2/2011 | Rey et al. |
| 8,131,370 B2 | 3/2012 | Janzig et al. |
| 8,250,752 B2 | 8/2012 | Drew |
| 8,504,172 B2 | 8/2013 | Chinn et al. |
| 2003/0040780 A1 | 2/2003 | Haeg et al. |
| 2003/0179536 A1 | 9/2003 | Stevenson et al. |
| 2004/0167582 A1 | 8/2004 | Tvaska et al. |
| 2006/0004419 A1 | 1/2006 | Olbertz |
| 2006/0047322 A1 | 3/2006 | Naviaux |
| 2007/0202728 A1 | 8/2007 | Olson et al. |
| 2007/0208381 A1 | 9/2007 | Hill et al. |
| 2008/0071320 A1 | 3/2008 | Brase |
| 2008/0246231 A1 | 10/2008 | Sjostedt et al. |
| 2008/0255631 A1 | 10/2008 | Sjostedt et al. |
| 2009/0017668 A1 | 1/2009 | Deininger et al. |
| 2009/0099620 A1 | 4/2009 | Rebentisch |
| 2009/0118778 A1 | 5/2009 | Biggs, Jr. et al. |
| 2009/0243756 A1 | 10/2009 | Stevenson et al. |
| 2009/0258519 A1 | 10/2009 | Dilmaghanian et al. |
| 2009/0312835 A1 | 12/2009 | Stevenson |
| 2010/0016928 A1 | 1/2010 | Zdeblick et al. |
| 2010/0109966 A1 | 5/2010 | Mateychuk et al. |
| 2010/0191299 A1 | 7/2010 | Ayzenberg |
| 2010/0274309 A1 | 10/2010 | Knipfer et al. |
| 2011/0029036 A1 | 2/2011 | Yamamoto et al. |
| 2011/0059639 A1 | 3/2011 | Dilmaghanian et al. |
| 2011/0071593 A1 | 3/2011 | Parker et al. |
| 2011/0137414 A1 | 6/2011 | Litzke et al. |
| 2011/0184479 A1 | 7/2011 | Kast et al. |
| 2011/0282410 A1 | 11/2011 | Lim |
| 2012/0253424 A1 | 10/2012 | Smith et al. |

FOREIGN PATENT DOCUMENTS

| | | |
|---|---|---|
| JP | 54057101 | 5/1979 |
| JP | 10223346 | 8/1998 |
| WO | 200064535 | 11/2000 |
| WO | 2005014108 | 2/2005 |
| WO | 2005105207 | 11/2005 |
| WO | WO2011011223 | 1/2011 |
| WO | 2011017432 | 2/2011 |

OTHER PUBLICATIONS

European Search Report; dated Apr. 17, 2013; Reference: PT02775EP; Applicant: Greatbatch Ltd.; Application No. EP 13151690.8-1652; Place of Search: Munich; Date of Completion of Search: Apr. 11, 2013.

European Search Report; Application No. EP 12 16 3521; Reference: PT02407EP; Application: Greatbatch Ltd.; Place of Search: Munich; Date of Completion of Search: Sep. 19, 2012.

* cited by examiner

FEED-THROUGH CONNECTOR ASSEMBLY FOR IMPLANTABLE PULSE GENERATOR AND METHOD OF USE

CROSS-REFERENCES TO RELATED APPLICATIONS

This application is a Continuation-in-Part of U.S. patent application Ser. No. 13/074,358, filed on Mar. 29, 2011, and incorporated herein by reference.

FIELD OF THE INVENTION

This application relates generally to a connector for a medical device and, more specifically, to a feed-through connector assembly for connecting to a connector assembly for achieving electrical contact with an Internal Pulse Generator.

BACKGROUND OF THE INVENTION

Medical devices have been implanted in patients to perform a variety of tasks. For example, programmable pulse generating systems are used to treat chronic pain by providing electrical stimulation pulses from an epidural electrode array placed near a patient's spine. Such Spinal Cord Stimulation (SCS) is useful for reducing pain in certain populations of patients. SCS systems typically include one or more electrodes connected to one or more connectors of an External Pulse Generator (EPG) or an Implanted Pulse Generator (IPG) via leads. In the case of an EPG, the lead must be connected to the EPG via an exit from the body. The pulse generator, whether internal or external, generates pulses that are typically delivered to the dorsal column fibers within the spinal cord through the electrodes which are implanted along or near the dura of the spinal cord. In a typical situation, the attached leads exit the spinal cord and are tunneled around the torso of the patient to a subcutaneous pocket where the IPG is implanted, or the wires exit the patient for connection to the EPG.

U.S. Pat. Nos. 7,537,474 and 6,895,876, incorporated herein by reference, disclose a connector solution for an implantable pulse generator (IPG) utilizing a coiled spring inside a contact block. The ends of the spring are welded together yielding a torus shape through which the in-line lead is inserted. The spring coils cant to conform to the contact ring of an IPG lead, thus making electrical contact. Each coil which contacts both the lead and the block forms a separate redundant electrical contact.

However, current connectors that could be used for connecting the IPG contacts to a connector assembly as disclosed herein have a number of shortcomings. First, support for IPGs with up to, or more than, 24-26 contacts has not been supported. Furthermore, previous connectors typically used hand routed feed through (FT) wires to connect directly to the lead connection stack so no FT connection was required when lead frame designs were employed (e.g. MDT Restore) the FT pitch was approximately 50% larger (~0.075") and no stress relief was required due to a much larger available weld area than would be desirable. Furthermore, it would be useful to provide IPG devices with multiple lead ports that have contact stacks that are assembled as a single unit, and tested in a single fixture before final assembly of the IPG, to determine that all channels have electrical continuity to inserted electrode pin(s) that represents a connection end of a stimulation lead.

SUMMARY OF THE INVENTION

Provided are a plurality of embodiments the invention, including, but not limited to, various designs for connector assemblies and their installation in medical devices.

For example, provided is a method for installing a connector assembly in a medical device including a plurality of conducting pins for connecting the medical device to a connector stack including a plurality of contact blocks, the method comprising the steps of:
  providing a connector assembly including a plurality of conductive leads each having a first end and a second end;
  fixedly connecting the first end of each one of the leads to corresponding ones of the conducting pins such that, at least for some portion of the conducting pins only non-consecutive ones of the conducting pins are connected to corresponding first ends of the leads and such that at least some pins are not connected to any first ends of the connector assembly; and
  fixedly connecting the second end of each one of the leads to corresponding ones of the contact blocks.

Also provided is a method for installing a connector assembly in a medical device including a plurality of conducting pins for connecting the medical device to a connector stack including a plurality of contact blocks, the method comprising the steps of:
  providing a connector assembly including a plurality of conductive leads each having a first end and a second end, the connector assembly having at least one temporary connecting structure connecting the plurality of leads together;
  fixedly connecting the first end of each one of the leads to corresponding ones of the conducting pins such that, for at least a portion of the conducting pins, only alternate ones of the conducting pins are connected to a corresponding first end of each one of the leads;
  fixedly connecting the second end of each one of the leads to corresponding ones of the contact blocks; and
  removing the temporary connecting structure from the plurality of conductive leads.

Further provided is a method for installing a connector assembly in a medical device including a plurality of conducting pins for connecting the medical device to a connector stack including a plurality of contact blocks, the method comprising the steps of:
  providing a connector assembly including a plurality of conductive leads each having a first end and a second end, the connector assembly having at least one temporary connecting structure connecting the plurality of leads together;
  fixedly connecting the first end of each one of the leads to corresponding ones of the conducting pins such that not all of the conducting pins are connected to a corresponding first end of the leads;
  fixedly connecting the second end of each one of the leads to corresponding ones of the contact blocks; and
  removing the temporary connecting structure from the plurality of conductive leads.

Also provided is a method for installing connector assemblies in a medical device including a plurality of conducting pins for connecting the medical device to a connector stack including a plurality of contact blocks, the method comprising the steps of:
  providing a first connector assembly including a first plurality of conductive leads each having a first end and a second end;

fixedly connecting the first end of each one of the leads of the first connector assembly to corresponding ones of the conducting pins such that not all of the conducting pins are connected to a corresponding first end of the first plurality of leads;

fixedly connecting the second end of each one of the first plurality of leads to corresponding ones of the contact blocks;

providing a second connector assembly including a second plurality of conductive leads each having a first end and a second end;

fixedly connecting the first end of each one of the leads of the second connector assembly to corresponding ones of the conducting pins that are not connected to any of the first plurality of leads; and fixedly connecting the second end of each one of the second plurality of leads to corresponding ones of the contact blocks different than the contact blocks connected to any of the first plurality of leads.

Provided is method for installing connector assemblies in a medical device including a plurality of conducting pins for connecting the medical device to a connector stack including a plurality of contact blocks, the method comprising the steps of:

providing a first connector assembly including a first plurality of conductive leads each having a first end and a second end;

fixedly connecting the first end of each one of the leads of the first connector assembly to corresponding ones of the conducting pins such that not all of the conducting pints are connected to one of the first plurality of leads;

fixedly connecting the second end of each one of the first plurality of leads to corresponding ones of the contact blocks;

providing a second connector assembly including a second plurality of conductive leads each having a first end and a second end;

fixedly connecting the first end of each one of the leads of the second connector assembly to corresponding ones of the conducting pins that are not connected to the first plurality of conductive leads such that at least some of the conducting pins connected to the first plurality of leads are interleaved or interspersed between some of the conducting pins connected to the second plurality of leads; and fixedly connecting the second end of each one of the second plurality of leads to corresponding ones of the contact blocks different than the contact blocks connected to the first plurality of leads.

Further provided is a method for installing connector assemblies in a medical device including a plurality of conducting pins for connecting the medical device to a connector stack including a first plurality of contact blocks supporting a first lead bore and a second plurality of contact blocks supporting a second lead bore, the method comprising the steps of:

providing a first connector assembly including a first plurality of conductive leads each having a first end and a second end;

fixedly connecting the second end of each one of the first plurality of leads to corresponding ones of the first plurality of contact blocks;

fixedly connecting the first end of each one of the first plurality of leads to corresponding ones of the conducting pins;

providing a second connector assembly including a second plurality of conductive leads each having a first end and a second end;

fixedly connecting the first end of each one of the leads of the second connector assembly to corresponding ones of the conducting pins different than the conducting pins connected to the first plurality of leads; and fixedly connecting the second end of each one of the second plurality of leads to corresponding ones of the second plurality of contact blocks.

Also provided is a method for installing a connector assembly in a medical device including a plurality of conducting pins for connecting the medical device to a connector stack including a plurality of contact blocks, the method comprising the steps of:

providing a connector assembly including a plurality of conductive leads each having a first end and a second end, the connector assembly having a first temporary connecting structure connecting the first ends of the plurality of leads together and a second temporary connecting structure connecting the second ends of the plurality of leads together;

fixedly connecting the first end of each one of the leads to corresponding ones of the conducting pins;

fixedly connecting the second end of each one of the leads to corresponding ones of the contact blocks;

removing the first temporary connecting structure; and removing the second temporary connecting structure, wherein the removals are to isolate each one of the conductive leads from each other during installation in the medical device.

Further provided is a method of installing a connector assembly in a medical device using any number of the above steps, and also provided is the connector assembly and/or the medical device of any of the above methods, among others.

Also provided are additional example embodiments, some, but not all of which, are described hereinbelow in more detail.

BRIEF DESCRIPTION OF THE DRAWINGS

The features and advantages of the example embodiments described herein will become apparent to those skilled in the art upon reading the following description, with reference to the accompanying drawings, in which.

DETAILED DESCRIPTION OF THE EXAMPLE EMBODIMENTS

Provided is a design for a welded feed through (FT) connector and its method of assembly and use that allows repeated flexing between a header and a hermetic enclosure of an active implantable medical device (e.g., an IPG) and minimizes stress to the electrical connection between the FT wire and the "lead frame" that leads to the contact stack for a stimulation lead. This is particularly important for welds made between dissimilar materials (e.g., Pt to MP35N or SS 316LVM) as these tend to have poorer mechanical attachment than those of similar materials (e.g., Pt to Pt).

The feed-through connection scheme described herein facilitates ease of assembly and long-term durability of a complete insert molded header to a hermetic enclosure containing an electronic stimulation circuit. The FT connector is especially designed for applications using laser welding of dissimilar materials such as platinum (Pt) IPG pins to MP35N or SS 316 LVM lead frame, but might also be useful for either similar material (e.g., Pt pins to Pt lead frame) or possibly resistance welding processes instead of laser welding.

Figure 1:
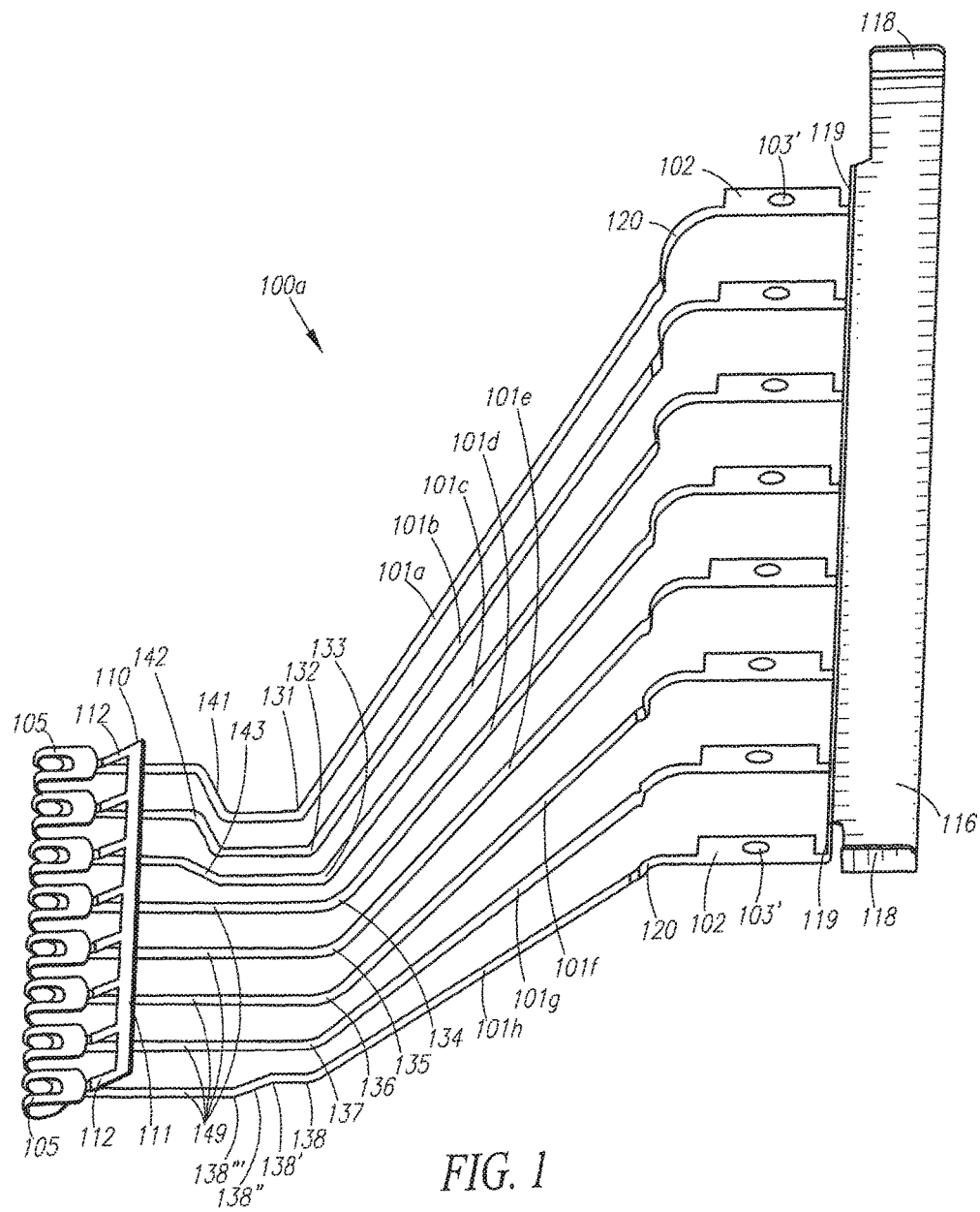
FIG. 1 shows an example embodiment of a first arrangement of a lead frame for use with an example IPG.
Figure 2:
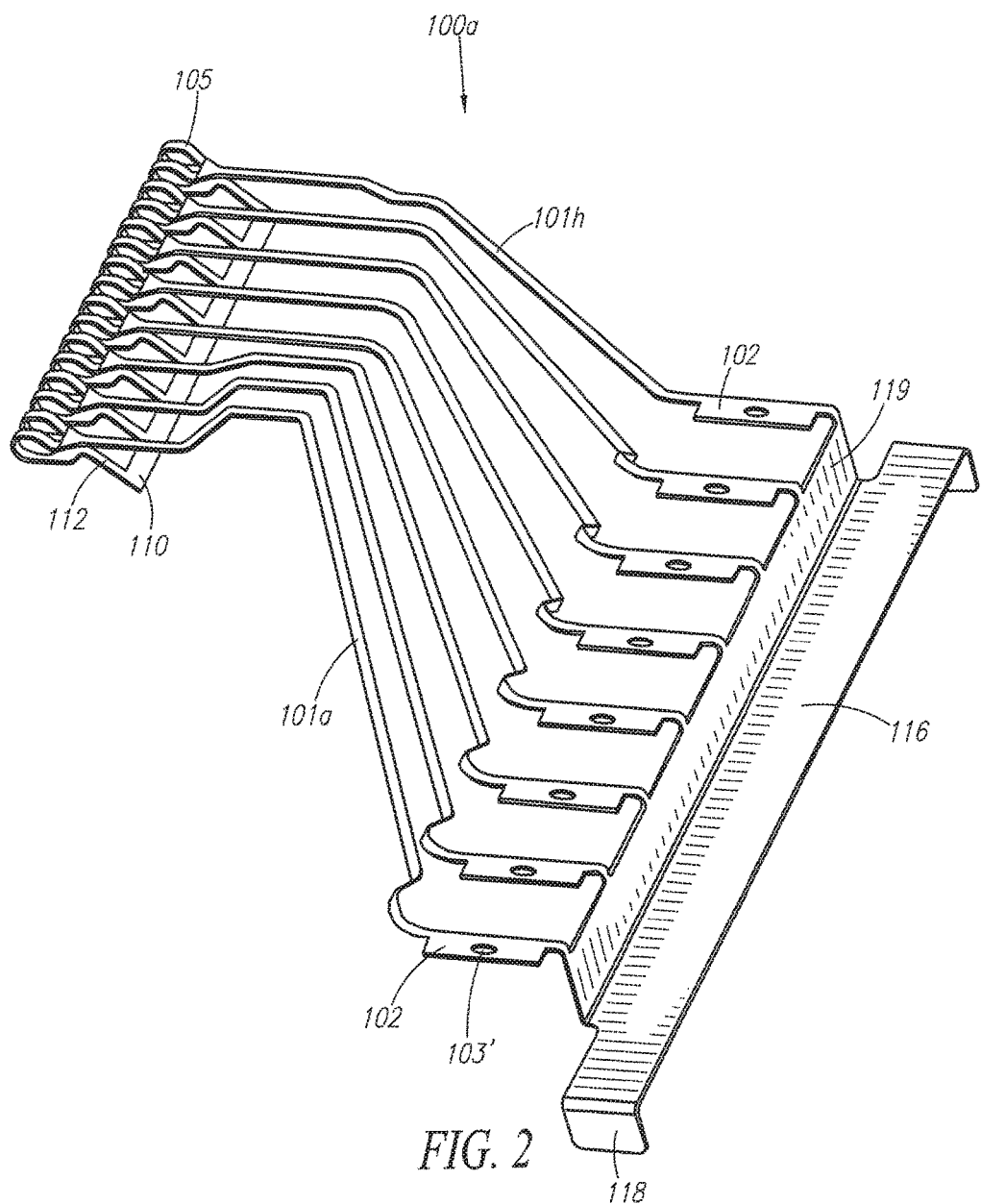
FIG. 2 shows another view of the lead frame of FIG. 1.

FIGS. 1 and 2 show different views of an example embodiment of a feed-through connector that can be used. The connector is arranged in a lead frame 100 after manufacture but before final use by connecting a plurality of leads 100 together by using a first temporary connecting structure 116 at one end of the lead frame 100 connected to the connector assembly connector lead end (CA lead end) 102 of each of the leads 101 at 119, and a second temporary connecting structure 110 connected to the IPG connector end (IPG end) 105 of each of the leads 101 at 112. Alternatively, as shown in FIG. 8 for a testing lead frame 100', the leads 101 can be connected together by using a web, such as an insulating web. The web structure in FIG. 8 is an embodiment used for testing and proof of concept, whereas the actual product would utilize the structure like that shown in FIGS. 1-2 and 7.

Figure 5:
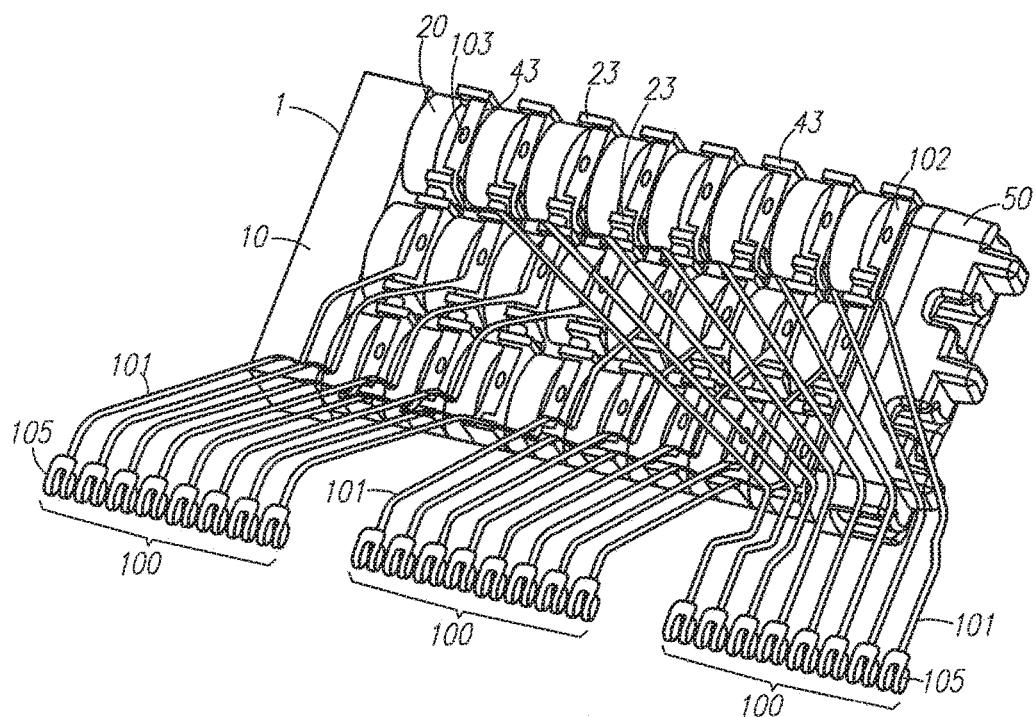
FIG. 5 shows the example contact assembly of FIG. 3 with connecting leads of three example arrangements of lead frames installed.

After installation, the temporary structures 116 and 110 can be removed, such as by breaking them off manually, for example. These structures would be made of the same materials as the lead frame itself, i.e., MP35N, Pt—Ir, or Stainless Steel, for example. The lead frame 100 has a plurality of leads 101 grouped together (as described above), such as into groups of 8 in the example embodiment. Typically, each lead frame 100 is formed into a shape to fit the contours of the IPG in which it will be installed. As shown in FIG. 5, each one of the three lead frames 100a, 100b, and 100c are formed with different routings and bendings of the leads 101 for connecting to a connector assembly 1.

For example, in the example embodiment of FIGS. 1 and 2, the leads 101 of lead frame 100 are formed into a particular shape for fitting as the rightmost lead frame 100a of FIG. 5. Each lead 101 (101a-101h) has a CA lead end 102 formed into a wider portion (tab) with a weld hole 103', the end 102 for connecting to a contact surface of a connector assembly by welding at weld hole 103' (described below). The CA lead ends 102 are all provided in a common plane for connecting to the connector assembly 1

The leads 101 are made narrower after the CA ends 102, and have a curved portion 120 formed to route the leads to fit the IPG assembly. A relatively long run in the leads 101 is provided until a second curved portion 131-138 is provided in corresponding leads 101, shown as 101a to 101h. As shown, each of the curved portions 131-138 of the eight shown leads 101a-101h has a different curvature, with the curve being much sharper the 131 on lead 101a and gradually being less sharp (i.e., having a larger radius of curvature) in consecutive curves 132-136 (leads 101b-101g), with lead 101g at 137 beginning to get sharper, and lead 101h actually has a first curve 138, a plateau portion 138' a second curve portion 138", and a third curve portion 138'".

After these curves leads 101d-101h have a relatively long flat portion 149, while three of the leads 101a-101c have additional curved portions to step the leads up. Finally, the IPG ends 105 on each of the leads 101 are provided in a common plane, each for connecting to the IPG connector pins 160 of the IPG 61, as shown in FIG. 7.

Figure 11:
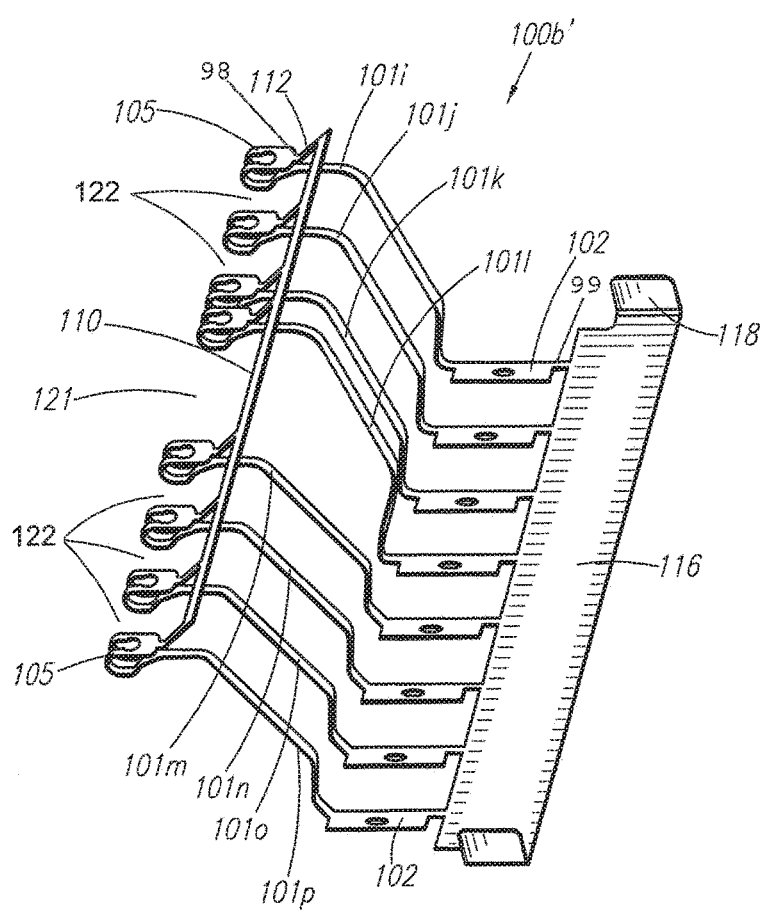
FIG. 11 shows the example embodiment of the second arrangement of a lead frame for use with the example IPG.
Figure 12:
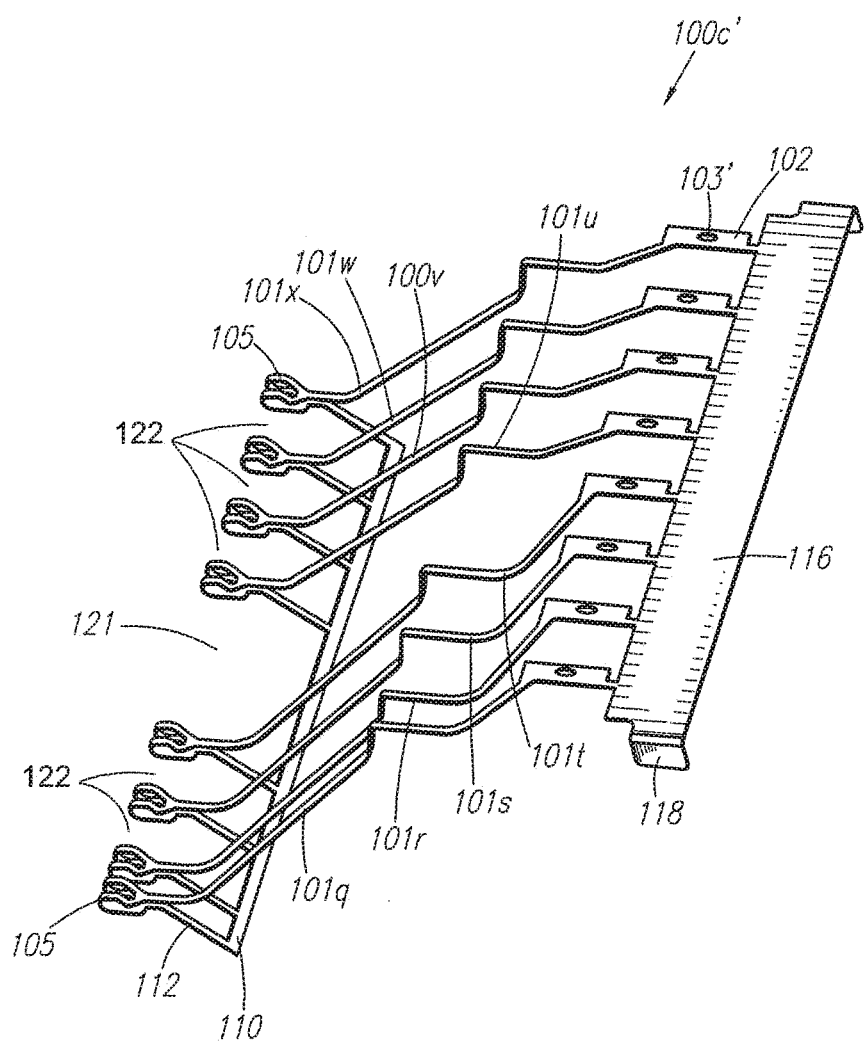
FIG. 12 shows the example embodiment of the third arrangement of a lead frame for use with the example IPG.

The other lead frames 100b' and 100c' are formed with leads routed differently in order to fit the contours within the IPG, as shown in FIGS. 11 and 12, as the specific routing is dependent on the design of the IPG and connector assembly, with the lead frame example routing described above merely being provided as an example to show the routing flexibility of the design. But as shown in FIG. 7, all of the IPG ends 105 are coplanar and the CA ends 102 are coplanar in the example implementation shown in that figure.

Figure 5A:
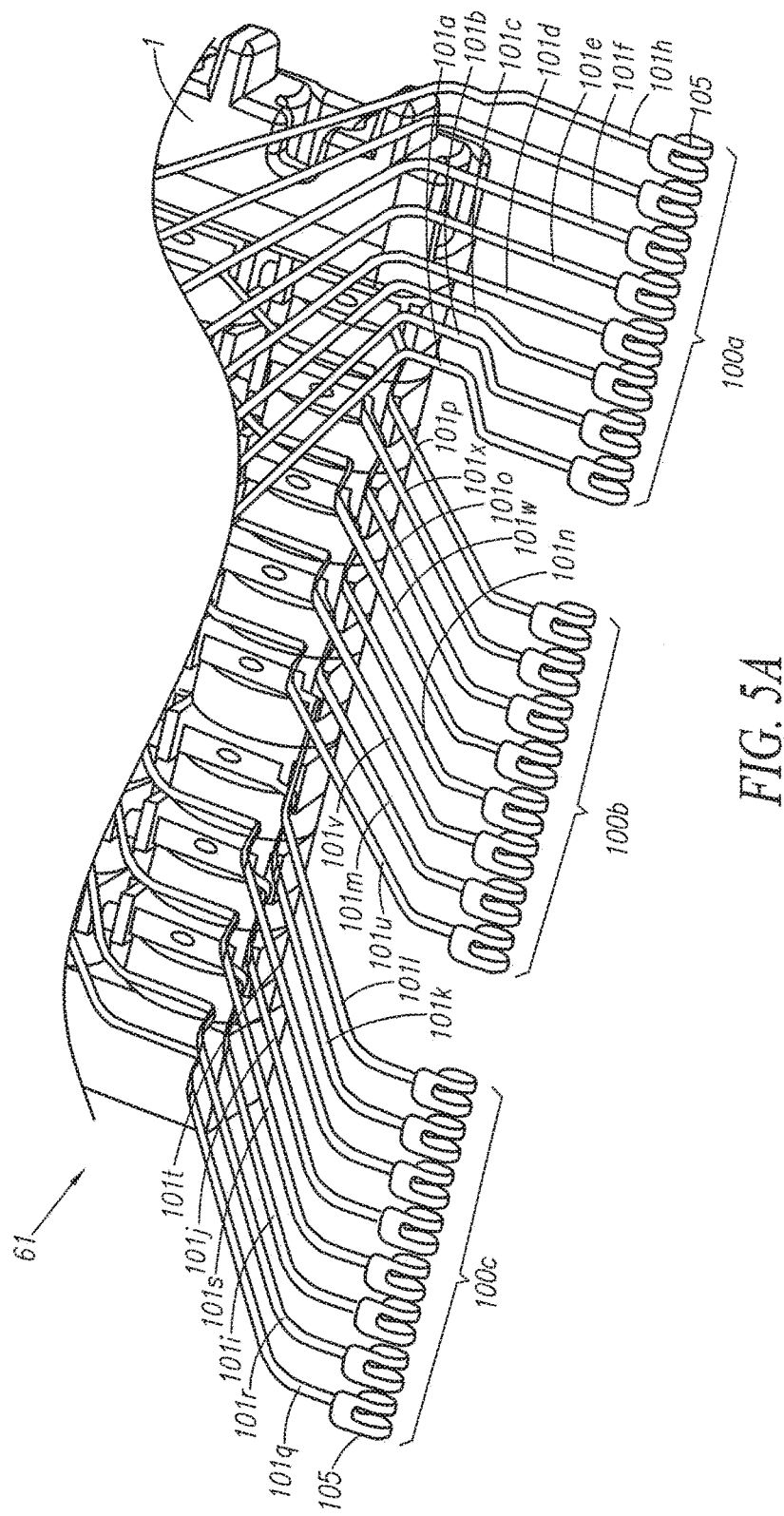
FIG. 5A shows a closeup of the example assembly of FIG. 5.

As shown in FIG. 5A, for the Example embodiment using the example IPG, the lead frames 100b' and 100c' of FIGS. 11 and 12 are installed in a manner that interleaves the leads 101i-101p of lead frame 100b' (FIG. 11) among some of the leads 101q-101x of lead frame 100c' (FIG. 12) into groupings 100b and 100c of FIG. 5A. Accordingly, the groupings 100b, 100c of the leads 101 shown in FIG. 5A do not correspond completely to the groupings of the individual leads of the lead frames 100b' and 100c' because of such interleaving, which "interleaves" some of the leads such that some of the leads of lead frame 100b' are provided in grouping 100c (i.e., leads 1011-1011) whereas some of the leads of lead frame 100c' are provided in grouping 100b (i.e., leads 101u-101x) in the manner illustrated in FIG. 5A. The gaps 122 between the leads of the lead frames 100b' and 100c' thus allow for such interleaving of the leads to allow room for pins 122a for connecting to other leads (see FIG. 11B), while the larger gaps 121 show where the leads transition from one grouping 100b to the other grouping 100c to allow for room for pins 121a for connecting to other leads (see FIG. 11B).

Figure 7:
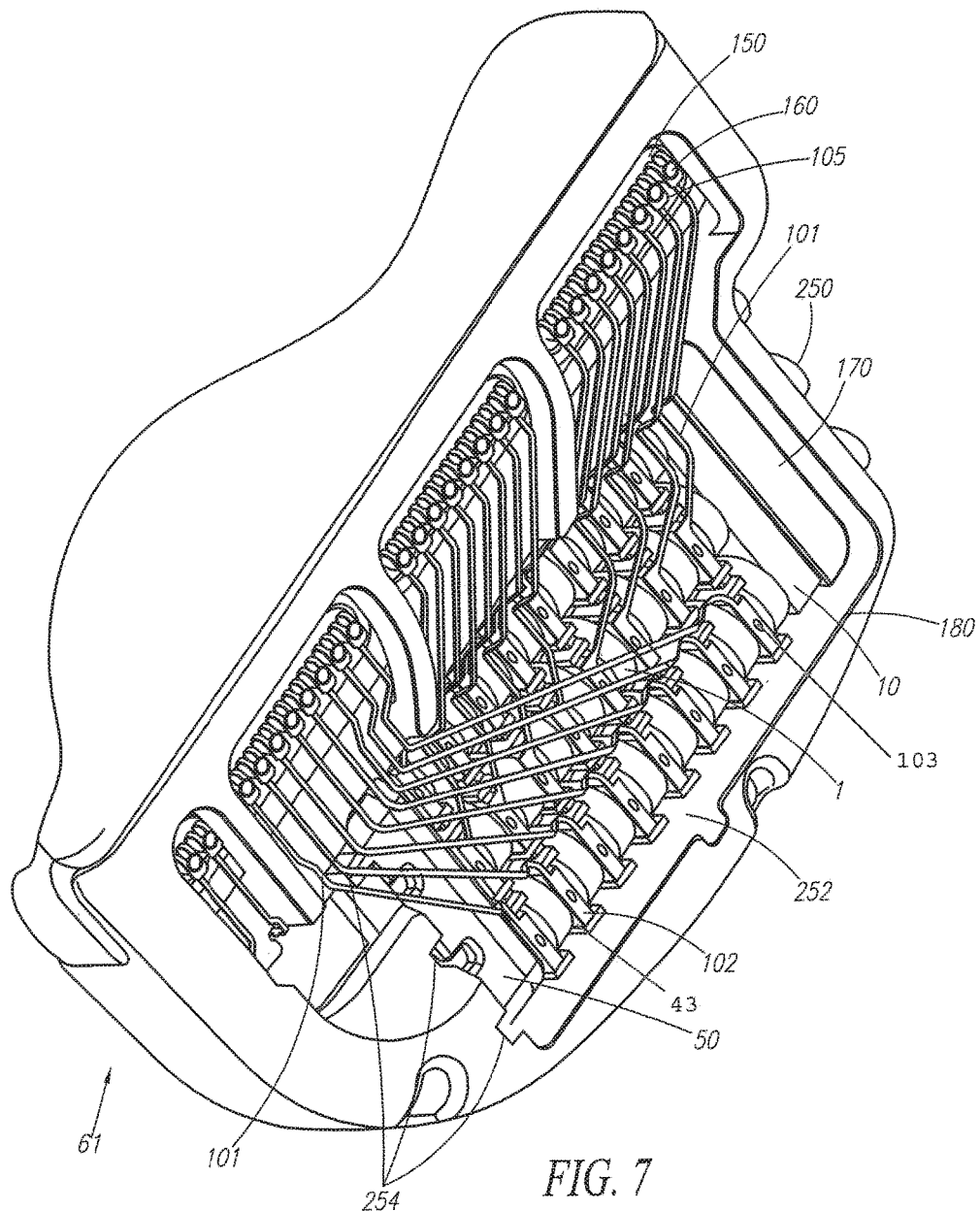
FIG. 7 shows an example embodiment of the contact assembly of FIG. 3 connected to an IPG.
Figure 8:
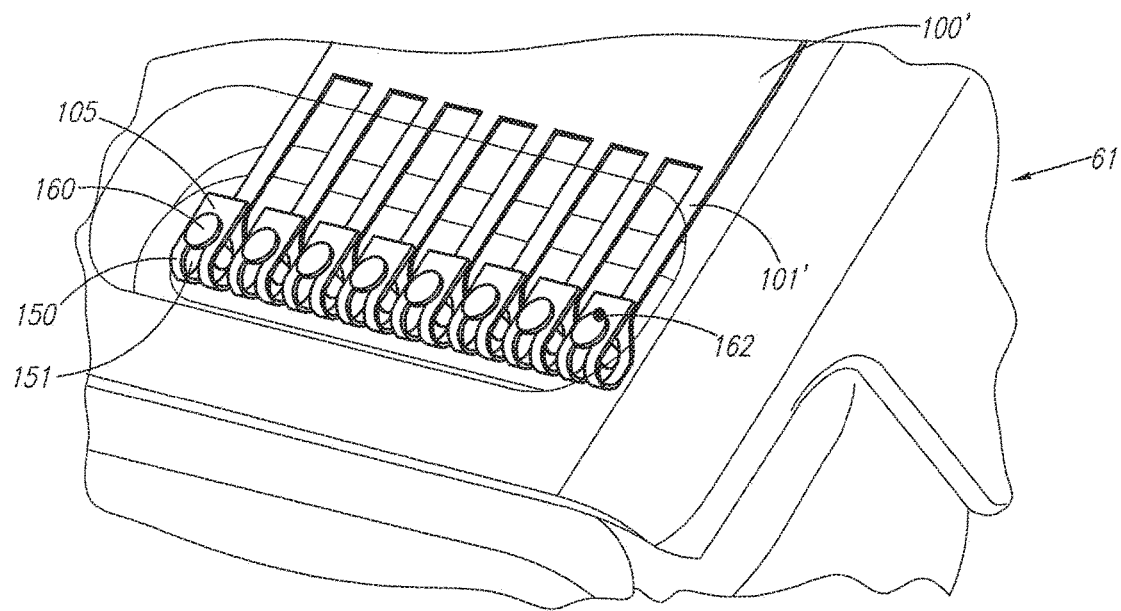
FIG. 8 shows a testing lead frame connected to the example IPG showing how the ends of leads of the lead frame may connect to corresponding IPG pins on the IPG.
Figure 9:
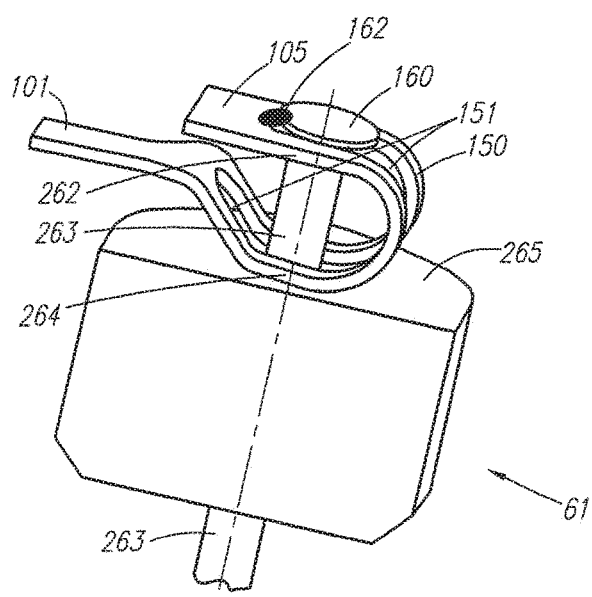
FIG. 9 shows a close up of how an example end of a lead of the example lead frame connects to an IPG pin of the example IPGs.

FIG. 8 shows a testing lead frame 100' with IPG lead ends 150 connected to an IPG 61 in the manner of the lead frame 100 (shown in FIG. 7). As shown in FIG. 9, the overall geometry and especially the U-shaped portion 150 of the IPG lead end 105 are configured to flex when the header is incidentally bent relative to the hermetic electronics enclosure of the IPG. This protects the welded portion of the connection from stress so that the mechanical integrity of the electrical connection is maintained. This benefit was clearly shown by a finite element analysis study of the proposed designs.

The weld 162 used for welding the IPG end 105 of the lead 101 to the IPG pin head 160 may or may not be provided on each of the ends 105, as desired. The flexing of the end 105 (described in more detail below) may be sufficient to ensure electrical connectivity between the IPG pin 160 and the lead 101 without requiring welding all of the IPG ends 105, but it is preferable to provide a 162 on each end 105 in order to ensure proper electrical connections and physical stability. If desired, multiple welds could be used on each end 105 to increase the reliability of the connection. In particular, two welds per end, provided opposite each other on the end 105 but in contact with the pin head 160, would be useful for additional structural strength and electrical connectivity. Or one continuous weld over the pin head 160 could be utilized instead of multiple welds.

Further referring to FIG. 9, it is shown that the IPG ends 105 have a flat portion 262 at the end of one branch of the U-shaped portion 150 for being placed against and electrically contacting the IPG pin head 160, and a second flat portion 264 at the end of the other branch of the U-shaped portion 150 for being placed against the ceramic portion 265 of the IPG. These flat portions 262, 264, in combination with the U-shaped portion 150, cooperate to compress the flat portions 262, 264 against the respective head/ceramic surfaces to keep the IPG end in compression, and thus in place, and ensuring, in combination with the welds 162, good electrical connectivity between the leads 101 and their respective IPG pins 263. As shown, the split section 151 in the end 105 accepts the pin body portion of the pin 263.

Figure 10:
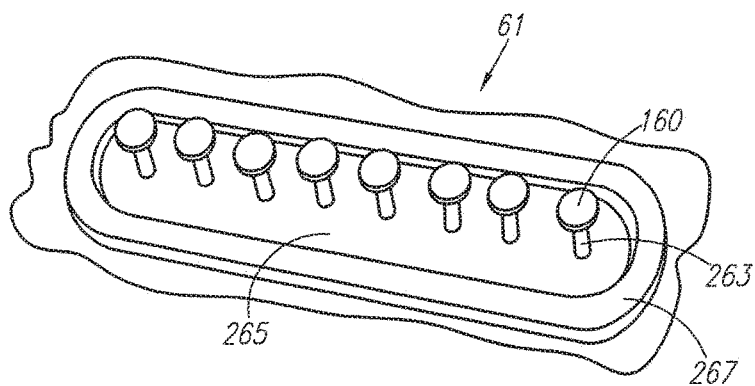
FIG. 10 shows an example arrangement of IPG pins on the example IPGs.

For the IPG 61 using the lead frame 100b' of FIG. 11, the assembly procedure proceeds as follows: The IPG ends 105 of lead frame 100b' (FIG. 11) are positioned on the IPG pin heads 160 (FIG. 10) such that the U-shaped portion of IPG end 105 is engaged as in FIG. 9. This is then accomplished for all IPG ends 105 of lead frame 100b'. The lead frame 100b' is then positioned so that all contact lead ends 102 lie directly upon conductive contact surfaces 43 of the contact blocks 40 (see FIG. 5) as depicted in FIG. 7. After this is accomplished, a weld joint 162 (FIG. 9) is executed on each of the IPG ends 105 in order to mechanically and electrically join all the IPG ends 105 to the pin heads 160. Next, welds are created at weld point 103 to join contact surface 43 to contact lead ends 102 (see FIG. 7). After welding lead frame 100b' in the manner the first and second temporary connecting structures 116, 110 are dissected at separation points 98 and 99, respectively, and removed, such as by manually bending and breaking them off, or by cutting them off with tools or lasers, for example. The similar process is repeated for the remaining lead frames, such as 100c' (FIG. 12) and 100a, to complete the lead frame attachment process for IPG 61. Analogous operations are performed to assemble lead frames to IPG 610, discussed below.

Figure 7A:
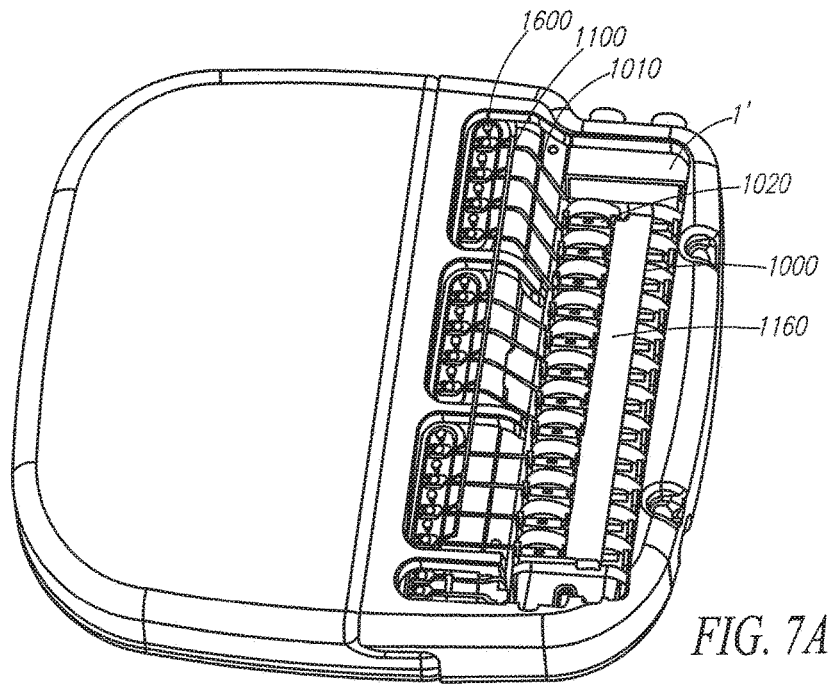
FIGS. 7A-7C shows various stages of assembly of another example embodiment of contact assemblies connected to another example IPG using two lead frames.
Figure 7B:
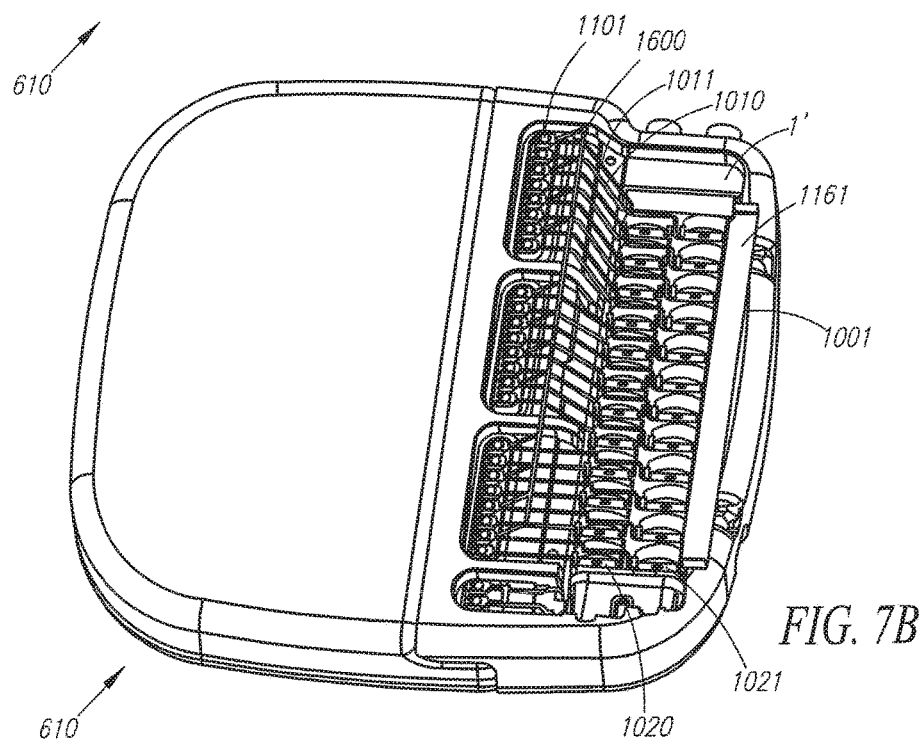
Figure 7C:
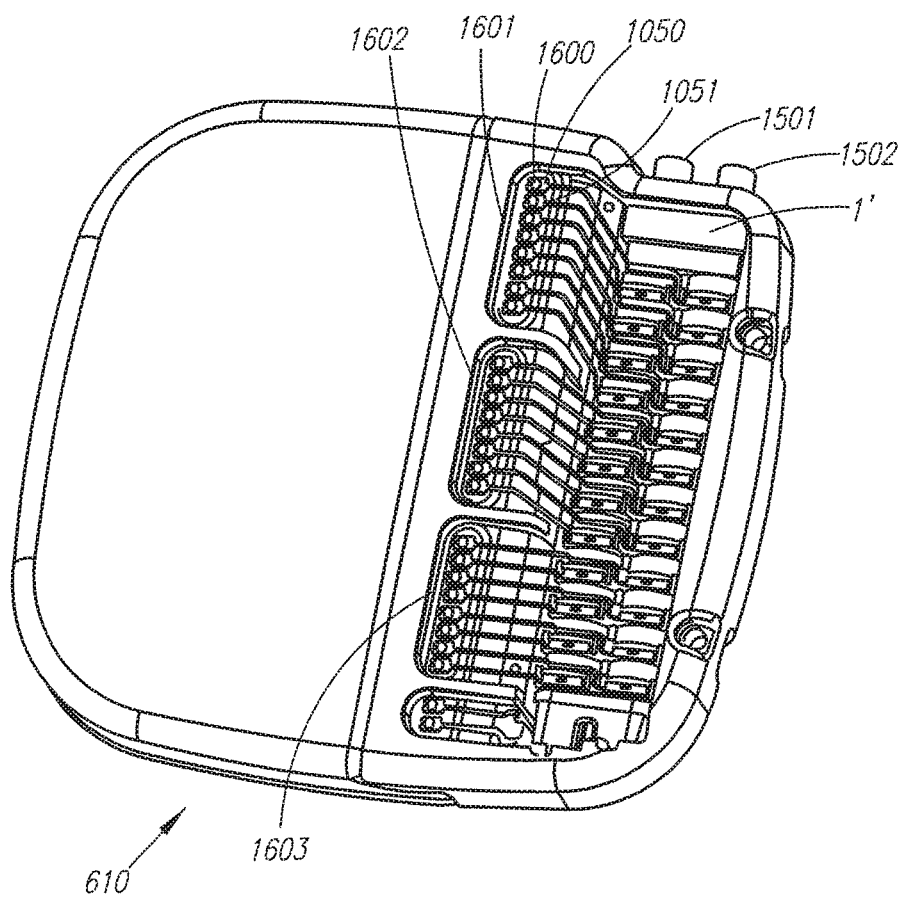

FIGS. 7A-7C show three views in various states of assembly of another example embodiment using an IPG 610 for use with two electrode pins supporting 24 channels, with 12 channels per pin. In this case, two lead frames 1000 and 1001, shown in FIGS. 11A and 12A respectively, are comprised by the IPG 610. This is in contrast to the IPG 61, which utilizes three lead frames during assembly. Thus, the assembly of IPG 610 is reduced by one lead frame insertion/assembly step.

Figures 11A, 12A:
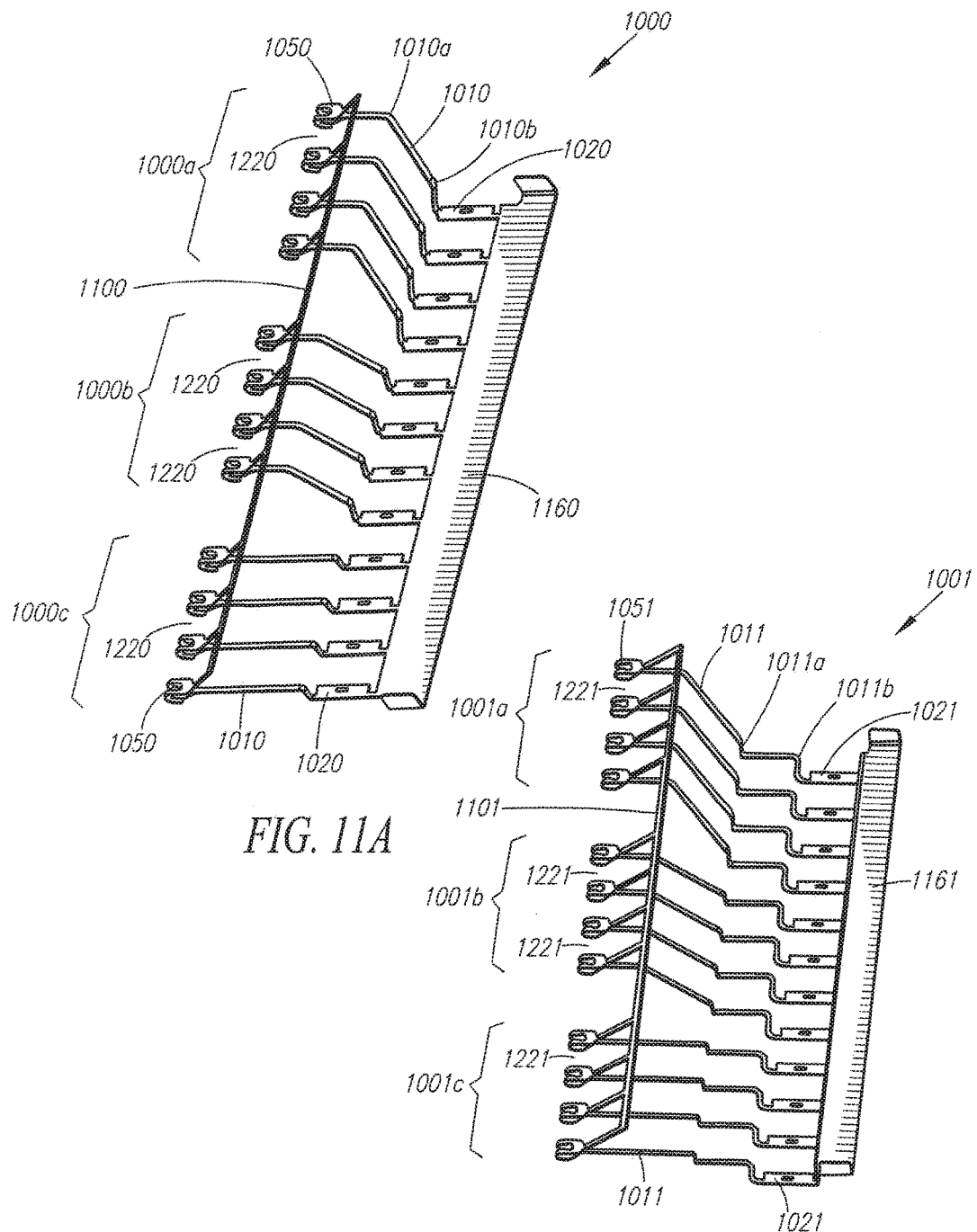
FIG. 11A shows an example embodiment of a first lead frame for use with the other example IPG.
FIG. 12A shows an example embodiment of a second lead frame for use with the other example IPG.
Figure 11B:
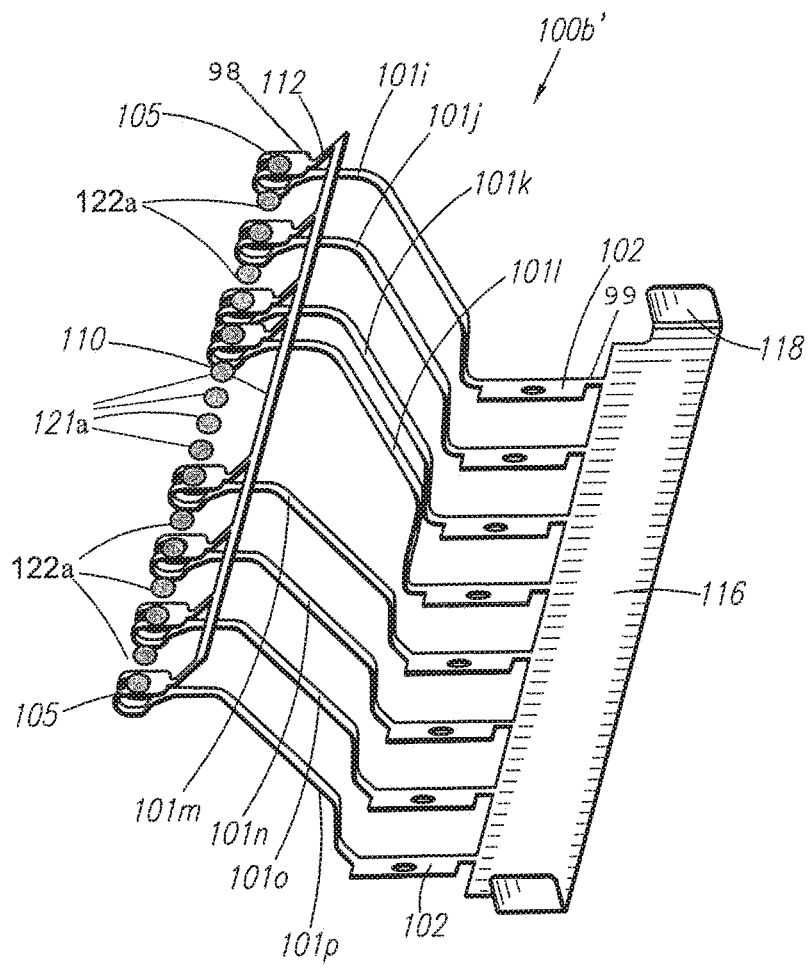
FIG. 11B shows the example embodiment of the second arrangement of a lead frame for use with the example IPG with pin placement shown.

The lead frame 1000 shown in FIG. 11A is likewise comprised of a plurality of lead ends 1020, an equal plurality of leads 1010 (some having bends such as 1010a and 1010b, for example), an equal plurality of IPG ends 1050 grouped by 1000a, 1000b, and 1000c, a first temporary connecting structure 1160, and a second temporary connecting structure 1100. The temporary connecting structures 1160, 1100 are used by an installer to insert the first lead frame 1000 into the IPG 610 as shown in FIG. 7A (in a manner as discussed above regarding IPG 61). Again, the leads 1010 have spaces 1220 between them that allow for additional leads to be interspersed in the manner shown in FIG. 7B using the second lead from 1001 into the IPG 610. The temporary connecting structures 1160/1100 are removed after the first lead frame.

Similarly, the second lead frame 1001 shown in FIG. 12A is comprised of a plurality of lead ends 1021, an equal plurality of leads 1011 (some having bends such as 1011a and 1011b, for example), an equal plurality of IPG ends 1051 grouped by 1001a, 1001b, and 1001c, a first temporary connecting structure 1161, and a second temporary connecting structure 1101. The temporary connecting structures are used by an installer to insert the first lead frame 1001 into the IPG 610 as shown in FIG. 7B (where lead frame 1000 is shown already installed) as discussed above. Again, the leads 1011 have spaces 1221 between them that allow for the leads 1010 of lead frame 1000 to be interspersed in the manner shown in FIG. 7B.

FIG. 7C then shows the final result IPG 610 with all temporary connecting structures having been removed. In other aspects this assembly is basically the same as discussed above with respect to IPG 61. Note that in the example IPG 610, each lead 1010 of the first lead frame 1000 is connected, via a lead end, to a contact block found in the same row of contact blocks that are associated with the electrodes of a first pin (entering at 1501), whereas each lead 1011 of the second lead frame 1001 is connected to respective contact blocks of the other row of contact blocks that are associated with the electrodes of a second pin (entering at 1052). But the IPG ends 1050 and 1051 of the respective lead frames are interspersed among each one of three sets 1601, 1602, and 1603 of pin heads 1600 provided on the IPG 610 for each one of the stimulation channels.

For installation into an example IPG 610, lead frame 1000 is first installed in a manner similar to that discussed for lead frame 100b', above. In this case, the lead ends 1050 of lead frame 1000 (FIG. 11A) are positioned on the IPG pin heads 1600 as shown in FIG. 7A such that the U-shaped portion 1050 is engaged in a similar manner as shown in FIG. 9. This is then accomplished for all lead ends 1050 of lead frame 1000 such that each lead end 1050 is installed on an alternate one of the pin heads 1600, as shown partially installed by FIG. 7A. Note that for this design, all lead frame lead ends 1020 are to be attached to all of the contact block contact surfaces that are closest to the IPG pins 1600 that are used to support a single lead bore 1501 (for accepting a single electrode pin, such as electrode pin 200), in consecutive order. Weld joints on ends 1050 and 1020 are executed as discussed regarding lead frame 100b'. Temporary connecting structures 1160, 1100 are then removed as discussed above regarding lead frame 100b'.

Similarly, lead frame 1001 is then installed such that lead ends 1051 are engaged with those alternating pin heads 1050 that are not engaged with lead frame 1000. Note that for this second lead frame 1001, all lead frame lead ends 1021 are to be attached to all of the contact block contact surfaces that are furthest from the IPG pins 1600 supporting another single lead bore 1502 (for accepting another electrode pin), again in consecutive order. Again, the proper weld joints are executed on ends 1051 and 1021, and the temporary connecting structures 1101 and 1161 are removed, completing the installation of the lead frames on IPG 610.

Although this installation example above discusses attaching the leads of a given lead frame to alternating conducting pin heads such that the leads of multiple lead frames are interleaved together (as shown in FIGS. 7A and 7B), other installation scenarios can be used, such as interspersing some of the leads (i.e., during installation, skipping some conducting pins for the leads of any given lead frame, such that the conducting pins are not all used consecutively for a given lead frame, but not necessarily in a pattern), as shown by the lead frames of FIGS. 11 and 12, where some leads are consecutive, but some skip conducting pins becoming interleaved, as shown by the gaps 122, representing no pattern. Furthermore, more than one consecutive conducting pin can be skipped when installing a lead frame, if desired. Such scenarios can be used to ease installation in complicated devices, for example, or for other reasons.

One advantage to the lead frame design discussed above for IPG 610, in addition to requiring the use and installation of one fewer lead frame, is that because each lead frame is installed on the pin heads in a regular manner (i.e., on alternating pin heads), there is little confusion as to which connections are required. Also, because all lead frame ends of a given lead frame attach to consecutive adjacent contact blocks, this also leads to a lesser chance of confusion on installation, making erroneous installations less likely.

Some of the advantages of these designs disclosed herein are:
1. Protects the welded joint 162 from stress due to flexing:
2. The assembly is self fixturing because of two features: Referring to FIGS. 7-9, the split section 151 in the U-shaped portion 150 of the IPG Lead ends 105 of the individual leads 101 of the lead frame 100/100' causes the individual connection features on the lead frame to self align with its respective IPG pin 263. When the U-shaped portion 150 of the IPG lead end 105 is dimensioned such that the parallel sides of the U are slightly more separated than the high dimensional limit of the space between the IPG ceramic portion 265 and the underside of the IPG pin head 160 the two elements are then positioned so as to provide intimate contact for the weld zone 162, a desirable condition for a successful weld.
3. The lead frame is further configured so that when the lead frame experiences distortion due to header bending, it remains clear of the FT flange 267 (see FIG. 10, which shows a partial view of an example arrangement of the IPG pins 263 on an IPG 61). This protects against the possibility of the leads 101 of the lead frame 100 making an electrical short to the FT flange 267.
4. The preceding benefits can all be accomplished at a compact spacing of 0.05" between the IPG pins 263, allowing for an IPG device with a higher number of contacts in a smaller overall device configuration that would otherwise be possible.

The lead frame can be utilized with a stack connector assembly that allows IPG devices with multiple lead ports to have contact stacks that are assembled as a single unit and tested in a single fixture before assembly to determine that all channels have electrical continuity to an inserted electrode pin that represents the connection end of a stimulation lead or plurality of such leads. FIG. 5 (described in more detail below) shows how the lead frame, with removable parts removed, would be connected to such a connector assembly 1.

Figure 3:
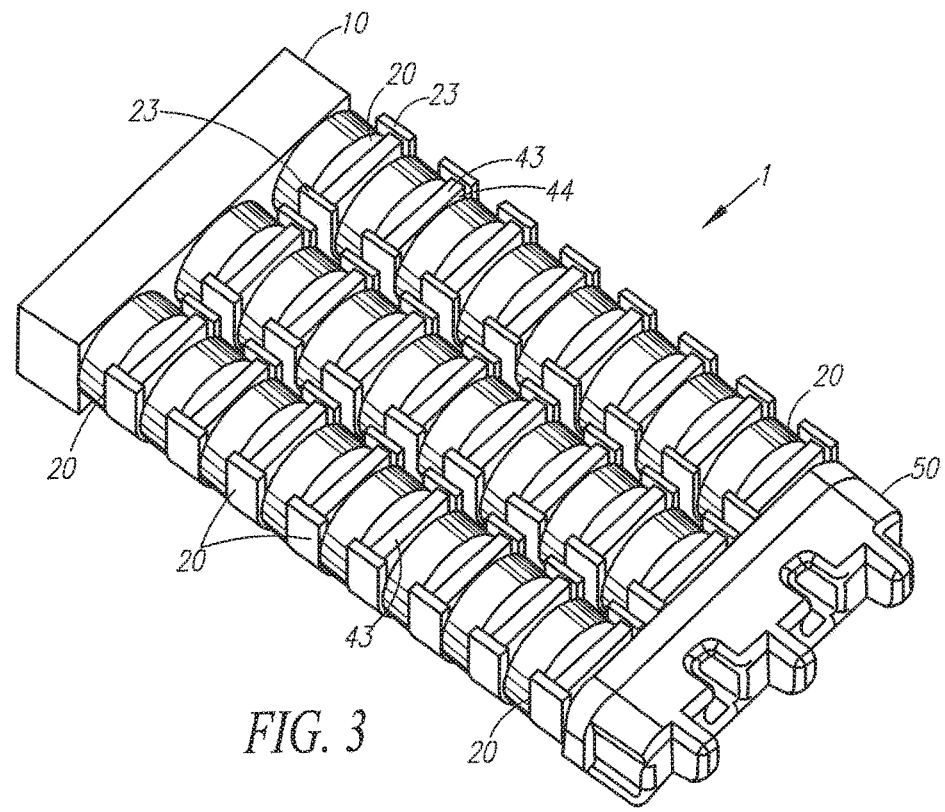
FIG. 3 shows an example embodiment of a contact assembly for use with the lead frame of FIG. 1.
Figure 4:
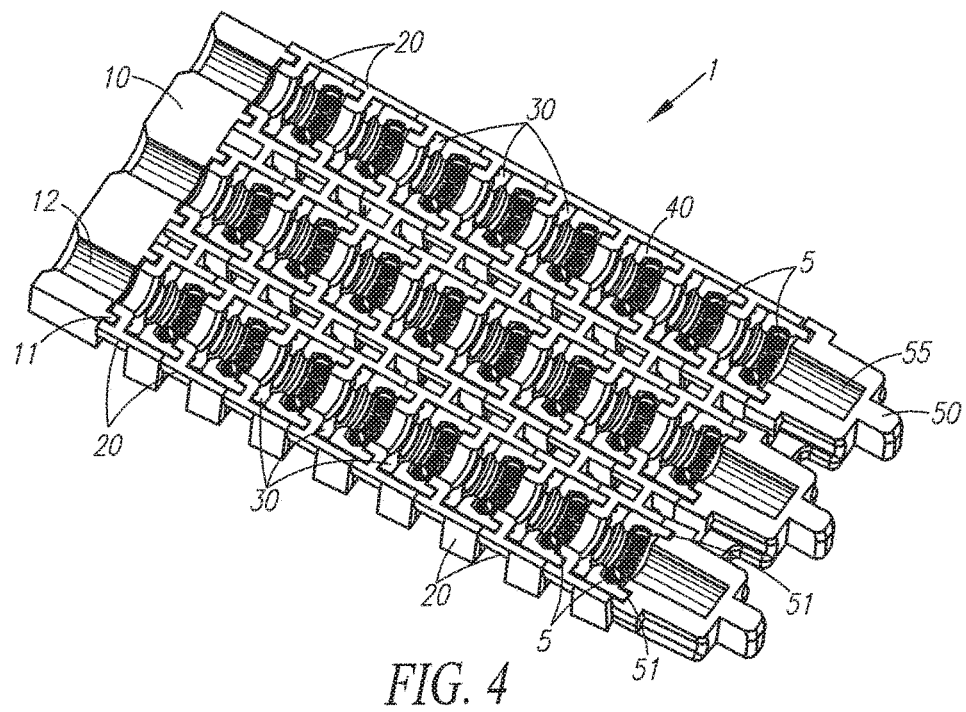
FIG. 4 shows a cross section of the example contact assembly of FIG. 3 flipped over.

FIG. 3 shows an example schematic of an example contact assembly that can be used with the lead frame discussed above. FIG. 4 shows a flipped cross section of the assembly of FIG. 3. The example contact assembly is comprised of a setscrew block 10 and an end cap 50 covering opposite ends of the contact assembly. A plurality of thermoplastic stacker components 20 are shown provided between the setscrew block 10 and the end cap 50. For the example embodiment, there is one stacker component per "row". Each of the thermoplastic stacker components is associated with a set of conductive contact blocks 40 (three per row are shown in the example embodiment, representing three "columns"), a set of corresponding seals 30 (3 per row in the example), and a set of contacts, such as springs 5 (again, 3 per row in the example). For this example embodiment shown in the figures, there are eight sets of stacker components (i.e., forming 8 "rows") with each stacker component (and thus each row) associated with a set of three contact block/seal/spring groupings (i.e., three "columns"). Of course, alternative embodiments could utilize alternative numbers of contact blocks (i.e., different numbers of rows), and each contact block might be associated with a different number of contact block/seal/spring groupings (i.e., different numbers of columns), such as using a single grouping, or two, four, five, or more groupings, depending on the desired implementation. Alternatively, the stacker components could be comprised of separate sub-components each associated with one of the contact blocks (hence for the example, there would be three sub-components).

The stacker component 20 has, for example, three open central portions including holes (bores), for receiving correspond electrode pins 200 as described below (see FIG. 6). For any given stacker component, each open central portion is adapted for receiving a corresponding seal 30. Each seal 30 has a hole 33 formed in its center that is aligned with an associated hole of the stacker component for receiving the corresponding electrode pin 200.

Each stacker component is adapted to receive, on one side, either a part of a contact block 40 or a part of a setscrew block 10, while another side is adapted to receive a part of another contact block 40 between two block tabs 23 of the stacker component 20.

Each contact block 40 has a conductive contact surface 43 on contact tab 44 that, when paired with the second side of an associated stacker component 40, is exposed between the associated pair of block tabs 23 of the stacker component, the conductive contact surface 43 being exposed for electrically connecting to a contact lead 102 (see FIG. 7). Each contact block 40 also has an interior hole and a hollowed out interior portion with a groove for holding a corresponding spring 5. Each spring 5 is formed in a ring (donut) shape of conductive material with a void in its center (for receiving the associated electrode pin 200) and is in electrical contact with its corresponding contact block to ensure electrically conductivity.

Figure 6:
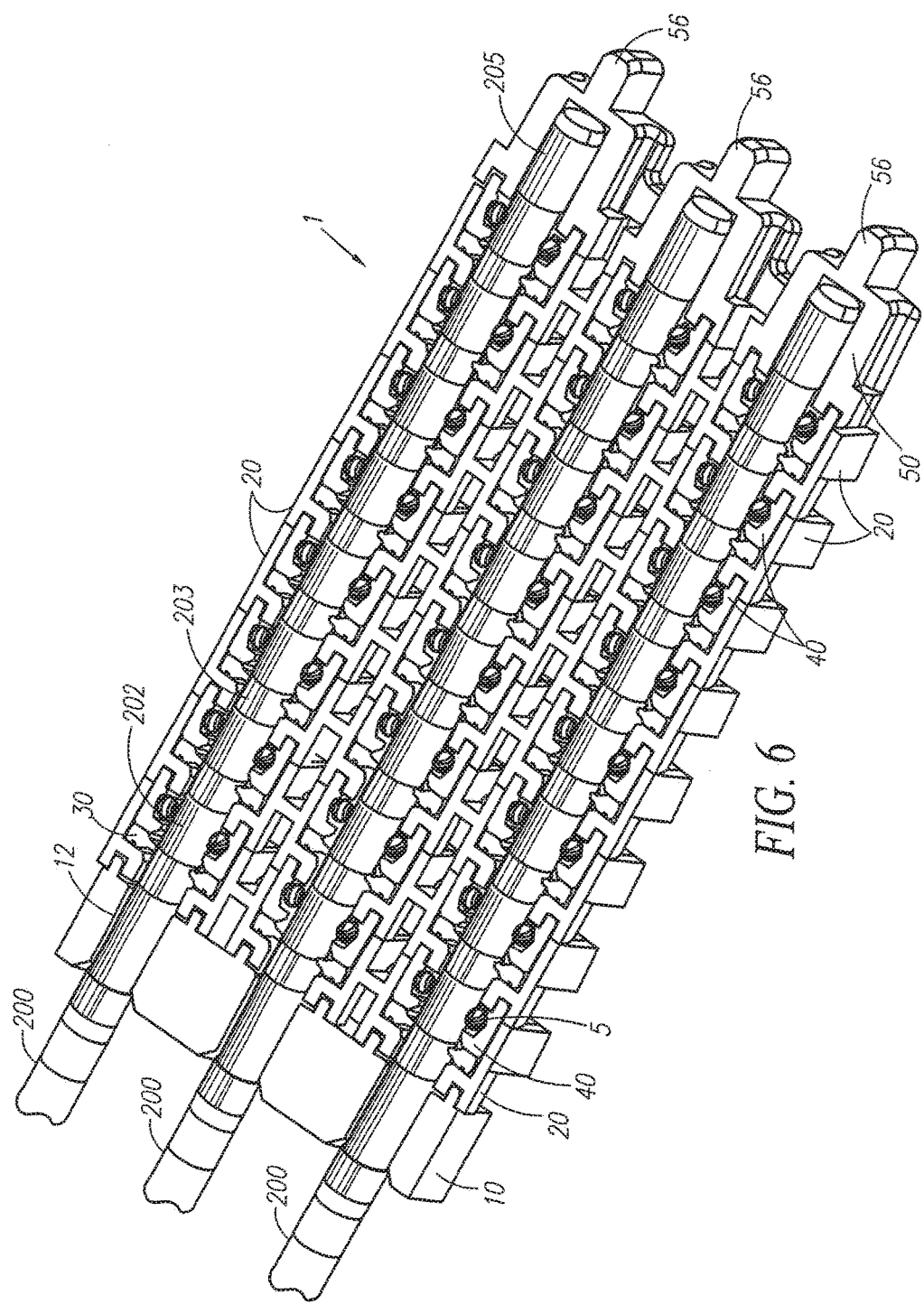
FIG. 6 shows the cross section of the contact assembly of FIG. 4 with example electrode pins installed therein.

The springs 5 are, in the example embodiment, torsion springs formed into a ring (a toroid/"donut" shape) having a space or hole in the center for receiving the corresponding electrode pin 200 (see FIG. 6). When the electrode pins 200 are inserted therethrough, the springs flex (cant) against and in electrical contact with a corresponding conductive surface portion, such as conductive ring 202 on the surface of the electrode pin 200 to make electrical contact with the conductive ring 202, as illustrated in FIG. 6. Alternative means of providing electrical contact between the electrode pin conductive rings 202 and the contact blocks could also be provided, such as by using metal tabs or different spring mechanisms, if desired, or integrating a contact structure directly in the contact block itself.

In most situations, each contact block is received by (mates with) a first side of a following stacker component 20 which acts to "cap" the components of a previous row assembled in the stacker component 20 and help hold them in place. The contact tab 44 fits between the block tabs 23, with the block tabs 23 extending beyond corresponding ends of the contact tab 44 and exposing a flat outer contact surface 43. If the contact block 40 is part of the last row of the device 1, the second cylindrical portion 42 is instead received by (mates with) the end cap 50.

Hence, for the example embodiment, each stacker component 20 is associated with a plurality (three each in the example embodiment) of seals 30, three contact blocks 40, and three springs 5, to create a row (layer).

FIG. 5 shows the contact assembly of the example embodiment connected to three sets (groups) of lead frames 100, each having 8 leads 101, with each lead 101 having an end 102 adapted for being attached to the exposed outer contact surface 43 of a corresponding contact tab 44 (see, e.g., FIGS. 3-4) and having a weld point 103. The leads 101 are conveniently routed in an organized manner around the tabs and other components of the stacker components to avoid shorting any of the leads together, such that each of the lead frames have leads that are routed differently from each other (as shown by the examples of FIGS. 1-2, versus the differently routed lead frames shown in FIGS. 10 and 11). Each of the leads 101 has a connector 105 at the other one end for connecting to a corresponding electrical connection point 160 on the IPG (as shown in FIG. 7). Thus, a conductive path is provided from one point 160 on the IPG, to the lead connector 105 connected to the point 160, down the associated lead 101 to the other end 102 to the corresponding contact block 40 to which the end 102 is connected, through the contact block to the associated spring 5 inserted therein, and on to the corresponding conductive ring 202, in contact with the spring 5, of the electrode pin 200 inserted through that contact block 40, and ultimately to an electrode, such as might be implanted near the spine of a patient for providing pulse therapy.

As shown in example of FIG. 6, three bores (columns) are defined through each of the eight rows of example contact assembly 1, with each of the bores/columns for receiving the corresponding one of the electrode pins 200 (thereby supporting three pins of eight conductors each). The pins are comprised of conductive rings 202 (each corresponding to one of the conductors of the electrode pin) and insulating portions 203. Because each pin supports a plurality of conductors, each pin can support a like plurality of electrodes for the desired medical therapy. Each of the bores is defined by the appropriate axial alignment of one of the holes 12 provided through the setscrew block 10, the hole (33) of one of the seals (30) in each row (inserted in its corresponding contact holder 25), and the hole (center) of one of the springs 5 (that are inserted in their corresponding of the contact block 40) in each row, and finally to one of the bores 55 of the end cap 50, in a manner sufficient to ensure that the electrode pins are adequately held in place and provide the appropriate electrical contacts to the associated contact blocks.

The setscrew block 10 is preferably comprised of titanium, although it could be comprised of any strong biocompatible metal such as stainless steel, nickel alloys, etc. The block can be manufactured using a machining process, or a metal injection molding (MIM) process, for example. The setscrew block holds setscrews (not shown) that tighten on the electrode pins 200 setscrew rings and prevent the leads from moving out of alignment with the contacts and seals of the contact assembly. The setscrew block 10 has a set of three screws (not shown) that are used to set (fix) the electrode pins 200 in place, once inserted, although other means of fixing the pins in place could be utilized, or the electrode pins may be kept in place solely by friction contact with the seals and springs through which they pass, or by some other mechanism.

Each of the stacker components 20 is preferably comprised of a polymer such as Polysulfone, but it could be any biocompatible polymer or other composition of similar capability. The components 20 can be manufactured by using Injection molding, or a machining process suitable for its composition and size. The stacker components 20 hold the seals 30 and contact blocks 40 in alignment (axially and radially), control seal compression, and act as a precision spacer to maintain contact to contact pitch. In the example embodiment, the stack pitch is about 0.100" nominal and accepts an electrode pin of about 0.055" nominal diameter. This concept will work down to around 0.080" pitch and pretty much any diameter (limited by how small the toroidal springs can be wound). The tolerance in the stacker contributes to the overall stack tolerance, likewise each of the seals is can be compressed as a separate assembly, so compression is controlled by the tolerances in one contact block and one seal not by the stack in its entirety.

Each of the seals 30 is preferably comprised of an elastic material such as silicone, or another elastomeric biocompatible polymer, and can be manufactured by molding, for example. Alternatively, the seals could be molded directly onto the stackers so they would form a single piece. The seals align with nonconductive segments 203 between the contact points on the electrode pin 200 and conform to the electrode pin surface so that even if flooded with conductive liquid in the lead bore, adjacent contacts have a sufficiently high enough impedance (i.e. 50 k Ohms) between them that they cannot effectively communicate electrically.

Each of the contact blocks 40 is preferably comprised of an MP35N alloy (a commercially available nonmagnetic, nickel-cobalt-chromium-molybdenum alloy that has a unique combination of properties), although any conductive biocompatible metal or alloy could be used. The contact blocks 40 can be manufactured by using a metal injection molding (MIM) process, or machined using known machining methods. The contact blocks are used to make electrical contact with the springs 5, transfer electrical signals from the electrode pins 200 to the leads 101, form a weld surface for the leads 101, and compress the seals 30 (in conjunction with the stackers components 20).

The springs 5 are comprised of a small diameter (e.g., 0.0035" or less) coiled Pt—Ir wire joined into a continuous toroidal shaped helix. The assembly can be made compatible with, and thus utilize, springs such as those disclosed in U.S.

Pat. Nos. 6,749,358 and 7,070,455, and U.S. Pat. App. Pub. No. 2008/0246231, incorporated herein by reference.

The end cap 50 is preferably comprised of the same or similar material discussed for the stacker components 20. Alternatively, the end cap 50 could be comprised of a biocompatible metal with the inclusion of additional seals to ensuring sealing, in particular where a conductive end cap might be desirable. The end cap forms the end of the pin bores and the depth of the holes 55 providing in the end caps (for receiving the end 205 of the electrode pins 200) registers the location where the electrode pins align with the rest of the stack.

The contact assembly 1 can be assembled on assembly pins, such as the electrode pins 200 or by using other pins of the appropriate size for aid in arranging the assembly components. For the example embodiment shown in the figures, one electrode pin is used through each one of the three bores. The pins help to maintain alignment in the stack and make the components and the stack easier to handle. For the example embodiment, the assembly is accomplished manually by hand, but could be automated where mass production is contemplated to cover the cost of the machine and robotics.

The assembled contact assembly with IPG pins therein is placed into a shell or housing 180. The shell has a feature (including the slots 254 of FIG. 7) that interlocks with the end cap tabs 56 on one side, including a vertical wall that forms a hard stop for the end cap 50. The other side of the shell 180 has an elastomeric piece 170 through which the bores continue through the cylinders 250. The assembly pins are inserted through the cylinders 250 of the elastomeric piece 170 first, then the curved and angled surfaces of the shell 180 and end cap 50 allow the rest of the stack to be pushed into place. Now the connector stack is trapped in alignment between the hard stop at the end cap 50 and the elastomeric piece 170 which serves as a spring to hold the stack in compression. The assembly pins can then be removed. The shell can then be attached to the IPG (or possibly was pre-attached). Then the lead frames 100 are attached to the IPG and the contact blocks, with the leads 101 being welded or soldered to the contact tab 43 at weld/solder point 103 (see FIG. 5). Then the shell is filled with a potting material 252, such as silicone, for example. The potting material 252 surrounds the contact assembly and each of the leads and the IPG connection points to insulate the contact assembly electrically and physically hold the components in alignment to one another and binds the assembly together.

Figure 13:
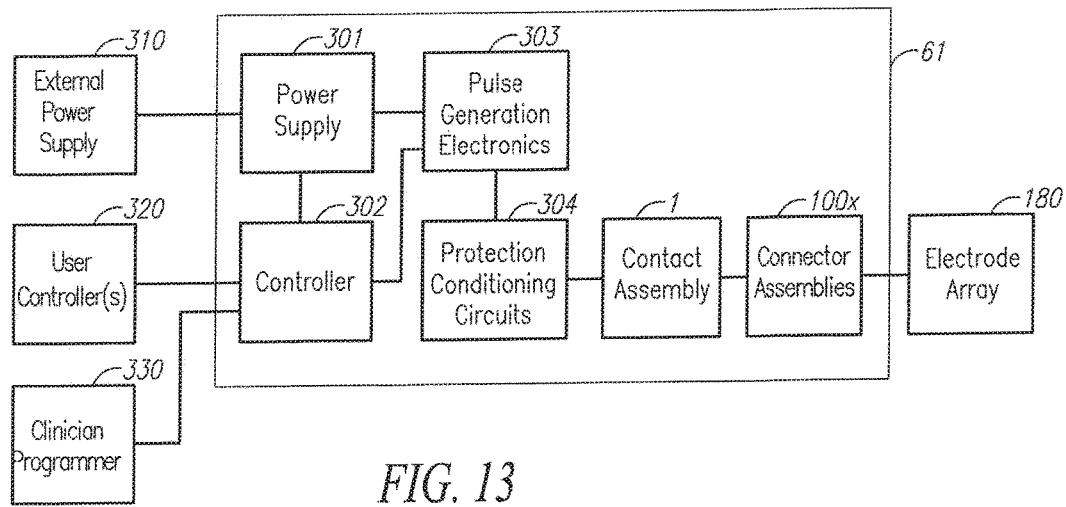
FIG. 13 is a block diagram showing example components of a pulse stimulation system using the example connector assembly including the example contact assembly and example lead frames.

FIG. 13 provides a block diagram of an example system including an IPG 61 that could utilized the contact assembly 1. The IPG 61 can be comprised of an internal power supply 301 (that may include a rechargeable battery), a controller 302, pulse generation electronics 303, protection/conditioning circuits 304, and the contact assembly 1 for connecting to an electrode array 180. The IPG 61 can be supported by an external power supply 310 (such as for charging the battery of the internal power supply 301), and a clinician programmer 330 and a user controller 320.

Figure 14:
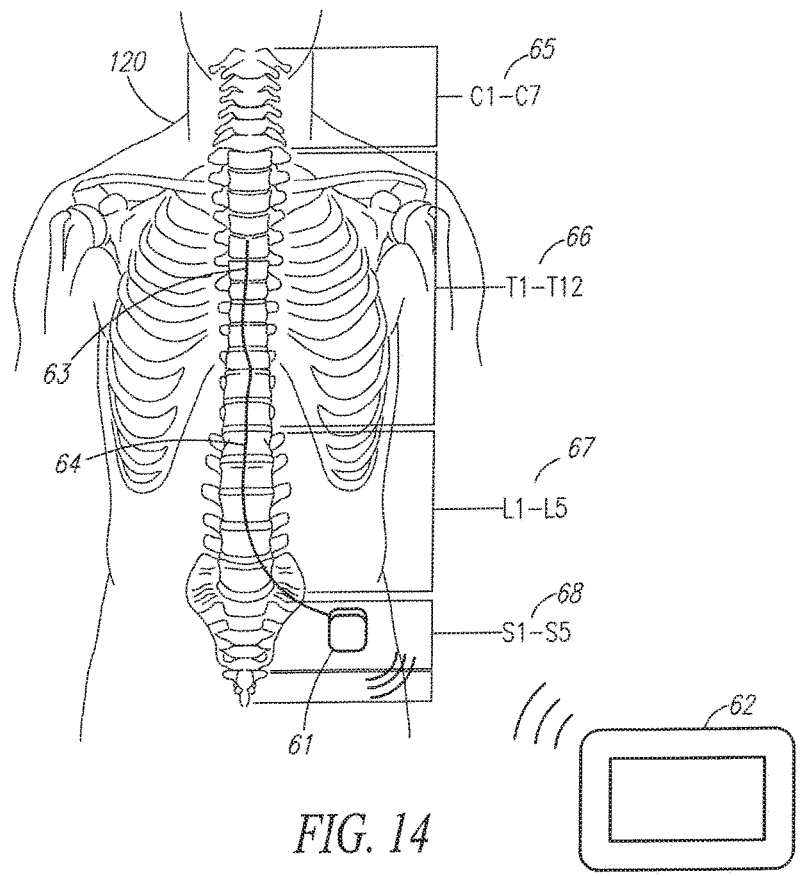
FIG. 14 is a diagram illustrating an example medical application of the pulse stimulation system of FIG. 13.

FIG. 14 shows an example application of the stimulator system for providing spinal stimulation. In that figure, the IPG 61 is shown implanted in a patient. Also shown is the human spine comprising the C1-C7 cervical vertebrae 65, the T1-T12 thoracic vertebrae 66, the L1-L5 lumbar vertebrae 67, and the S1-S6 sacral vertebrae 68. Electrodes 63 are shown disposed at the distal end of the spine and are positioned near the thoracic vertebrae 66. The Electrodes 63 are attached to the IPG 61 via electrode leads 64.

The leads and electrodes may be positioned anywhere along the spine to deliver the intended therapeutic effects of spinal cord electrical stimulation in the desired region of the spine. The distal end of the lead with its accompanying electrodes may be located along the epidural space and adjacent a desired portion of the spinal cord using well-established and known techniques for implanting and positioning SCS leads and electrodes, and the IPG 61 may be programmed using a clinician or other type of programmer 62 (such as a patient controller), as desired (and further described above). The electrode leads 64 can be connected to the IPG via a contact assembly as described in this application.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method for installing a first connector assembly in a medical device including a plurality of conducting pins for connecting the medical device to a connector stack including a plurality of contact blocks, the method comprising:
    a) providing the first connector assembly including a plurality of conductive leads each having a first end and a second end;
    b) fixedly connecting the first end of each one of the leads to corresponding ones of the conducting pins such that, at least for some portion of the conducting pins only non-consecutive ones of the conducting pins are connected to corresponding first ends of the leads and such at least some pins are not connected to any first ends of the first connector assembly; and
    c) fixedly connecting the second end of each one of the leads to corresponding ones of the contact blocks,
        wherein at least some of said conducting pins not connected to leads of the first connector assembly are connected to one or more leads of a second connector assembly in the medical device.

2. The method of claim 1, wherein the first connector assembly has at least one temporary connecting structure connecting the plurality of leads together that is removed as the first connector assembly is installed in the medical device.

3. The method of claim 1, wherein the first connector assembly has a first temporary connecting structure connecting the first ends of the plurality of leads together, and a second temporary connecting structure connecting the second ends of the plurality of leads together, wherein the first and second temporary connecting structure are removed as the first connector assembly is installed in the medical device.

4. The method of claim 3, wherein the fixedly connecting comprises the step of welding to accomplish the fixedly connecting, and wherein the temporary connecting structures are removed after the welding.

5. The method of claim 1, wherein the fixedly connecting comprises the step of welding to accomplish the fixedly connecting.

6. The method of claim 1, wherein the plurality of contact blocks are provided on a single bore of the medical device for supporting an electrode pin.

7. A method for installing a connector assembly in a medical device including a plurality of conducting pins for connecting the medical device to a connector stack including a plurality of contact blocks, the method comprising:
 a) providing the connector assembly including a plurality of conductive leads each having a first end and a second end, the connector assembly having at least one temporary connecting structure connecting the plurality of leads together;
 b) fixedly connecting the first end of each one of the leads to corresponding ones of the conducting pins such that, at least for a portion of the conducting pins, only alternate ones of the conducting pins are connected to corresponding first ends of the leads;
 c) fixedly connecting the second end of each one of the leads to corresponding ones of the contact blocks; and
 d) removing and discarding the temporary connecting structure from the plurality of conductive leads.

8. The method of claim 7, wherein the fixedly connecting comprises the step of welding to accomplish the fixedly connecting.

9. The method of claim 7, further comprising a second temporary connecting structure for connecting the first ends or the second ends of the conductive leads together.

10. The method of claim 7, wherein the plurality of contact blocks are provided on a single bore of the medical device for supporting an electrode pin.

11. A method for installing a connector assembly in a medical device including a plurality of conducting pins for connecting the medical device to a connector stack including a plurality of contact blocks, the method comprising:
 a) providing the connector assembly including a plurality of conductive leads, each having a first end and a second end, the connector assembly having at least one temporary connecting structure connecting the plurality of leads together;
 b) fixedly connecting the first end of each one of the leads to corresponding ones of the conducting pins such that not all of the conducting pins are connected to a corresponding first end of the leads;
 c) fixedly connecting the second end of each one of the leads to corresponding ones of the contact blocks; and
 d) removing and discarding the temporary connecting structure form the plurality of conductive leads.

12. The method of claim 11, wherein the fixedly connecting comprises the step of welding to accomplish the fixedly connecting.

13. The method of claim 11, further comprising a second temporary connecting structure for connecting the first ends or the second ends of the conductive leads together.

14. The method of claim 11, wherein said plurality of contact blocks are provided on a single bore of the medical device for supporting an electrode pin.

15. The method of claim 1, further comprising a temporary connecting structure for connecting the first ends or the second ends of the first plurality of conductive leads together, wherein the temporary connecting structure is removed as the first connector assembly is installed in said medical device.

16. The method of claim 11, further comprising another temporary connecting structure for connecting the other of the first ends or the second ends of the first plurality of conductive leads together, wherein the temporary connecting structure are removed as the connector assembly is installed in the medical device.

17. The method of claim 11, wherein the contact blocks to which the second end of the first plurality of leads are fixedly connected are provided on a single bore of the medical device for supporting an electrode pin.

18. The method of claim 11, wherein the contact blocks to which the second end of the first plurality of leads are fixedly connected are distributed among more than one bore of the medical device for supporting a plurality of electrode pins.

19. The method of claim 11, wherein a plurality of the conducting pins connected to the plurality of leads are interleaved or interspersed with a plurality of the conducting pins connected to a second plurality of leads of a second connector assembly.

20. The method of claim 1, further comprising the steps of:
 providing the second connector assembly including a second plurality of conductive leads each having a first end and a second end;
 fixedly connecting said first end of each one of said leads of said second connector assembly to corresponding ones of said conducting pins that are not already connected to any leads; and
 fixedly connecting said second end of each one of said second plurality of leads to corresponding ones of said contact blocks different than the contact block connected to any of said first plurality of leads.

21. The method of claim 7, further comprising the steps of:
 providing a second connector assembly including a second plurality of conductive leads each having a first end and a second end, the second connector assembly having at least one temporary connecting structure connecting the plurality of leads together;
 fixedly connecting said first end of each one of said leads of said second connector assembly to corresponding ones of said conducting pins that are not already connected to any f leads;
 fixedly connecting said second end of each one of said second plurality of leads to corresponding ones of said contact blocks different than the contact blocks connected to any of said first plurality of leads; and
 removing the temporary connecting structure of the second connector assembly from the second plurality of conductive leads.

* * * * *

UNITED STATES PATENT AND TRADEMARK OFFICE
CERTIFICATE OF CORRECTION

PATENT NO. : 9,931,513 B2
APPLICATION NO. : 13/359954
DATED : April 3, 2018
INVENTOR(S) : Daniel N. Kelsch and Alexander K. Smith It is certified that error appears in the above-identified patent and that said Letters Patent is hereby corrected as shown below:

In the Specification
Column 1, Line 60, "(~0.075")" should be --(~0.75")--.
Column 6, Line 34, "138"''" should be --"138"--.
Column 6, Line 61, "1011-1011" should be --101$i$-101$l$--.
Column 9, Line 66, "0.05" should be --.05--.
Column 12, Line 32, "0.100" should be --.100"--.
Column 12, Line 33, "0.055" should be --.055"--.
Column 12, Line 34, "0.080" should be --.080"--.
Column 12, Line 65, "0.0035"" should be --.0035"--.

In the Claims
Column 16, Line 51, delete "f".

Signed and Sealed this
Second Day of July, 2019

Andrei Iancu
*Director of the United States Patent and Trademark Office*